(12) United States Patent
Lee et al.

(10) Patent No.: US 9,211,353 B2
(45) Date of Patent: Dec. 15, 2015

(54) CLARIFIER FOR BIDET WITH PHYTONCIDE FILTER

(71) Applicant: DAELIM B&CO CO., LTD., Changwon-si (KR)

(72) Inventors: Jong Won Lee, Seoul (KR); Jong-Hoon Park, Seoul (KR); Jun-Kyung Kwon, Incheon-si (KR); Yun-Deok Nam, Incheon-si (KR)

(73) Assignee: DAELIM B&CO CO., LTD. (KR)

( * ) Notice: Subject to any disclaimer, the term of this patent is extended or adjusted under 35 U.S.C. 154(b) by 315 days.

(21) Appl. No.: 13/861,864

(22) Filed: Apr. 12, 2013

(65) Prior Publication Data

US 2013/0280136 A1    Oct. 24, 2013

(30) Foreign Application Priority Data

Apr. 19, 2012 (KR) .................. 10-2012-0040747
Mar. 26, 2013 (KR) .................. 10-2013-0032296

(51) Int. Cl.
*A61L 9/12* (2006.01)
*E03D 9/05* (2006.01)
*A61L 2/20* (2006.01)
*A61L 9/013* (2006.01)

(52) U.S. Cl.
CPC . *A61L 2/20* (2013.01); *A61L 9/013* (2013.01); *A61L 9/12* (2013.01)

(58) Field of Classification Search
CPC ........... A61L 9/013; A61L 9/12; E03D 9/005; E03D 9/04
USPC .............. 422/124; 4/209 FF, 213, 209 R, 309
See application file for complete search history.

(56) References Cited

U.S. PATENT DOCUMENTS

2007/0130684 A1    6/2007    Watts
2008/0098899 A1 *  5/2008    Uchida et al. ................ 96/255
2008/0299014 A1 * 12/2008    Kim ............................. 422/124

FOREIGN PATENT DOCUMENTS

| CN | 2136038 | 6/1993 |
| KR | 200351641 | 5/2004 |
| KR | 200403266 | 12/2005 |
| KR | 1020110038941 | 4/2011 |

OTHER PUBLICATIONS

Chinese Office Action—Chinese Application No. 2013101384606, issued on Dec. 2, 2014, citing KR 20-0351641 and KR 20-0403266.

* cited by examiner

*Primary Examiner* — Sean E Conley
*Assistant Examiner* — Donald Spamer
(74) *Attorney, Agent, or Firm* — Cantor Colburn LLP

(57) ABSTRACT

Disclosed is a filtering device for a bidet, including a base, a blower sucking air into the bidet, a filter casing mounted to the base, a phytoncide filter unit contained in the filter casing, a door opening and closing the filter casing, and a duct connecting the blower and the filter casing.

4 Claims, 8 Drawing Sheets

CLARIFIER FOR BIDET WITH PHYTONCIDE FILTER

BACKGROUND OF THE INVENTION

1. Field of the Invention

The present invention relates, in general, to a clarifier for bidet with phytoncide filter, which uses a phytoncide filter unit to provide bad smell removal/deodorization and anti-bacterial/insect-proof functions, etc. in a bidet, as well as to provide a user with a pleasant feeling.

2. Description of the Related Art

As disclosed in the Applicant's related Patent Documents, a deodorization device for a bidet has a structure in which a deodorizing filter unit is detachably attached to a lower housing thereof so as to filter air in the bidet therethrough and discharge the filtered air to the outside of the bidet.

Here, the deodorizing filter unit is detachably attached into a through-hole formed in the lower housing of the bidet. The through-hole is formed at the side of the lower housing.

In the case where the through-hole is formed at the side of the lower housing, a container for a cleaning solution and a nozzle are separated far apart from each other, so a feeding hose is needed to feed the cleaning solution from the container to the nozzle.

The through-hole is opened and closed by a door. The door is provided with a plurality of air vents. The door has an inside recess in which the deodorizing filter unit is installed.

When the deodorizing filter unit is replaced with a new one, the door is removed from the through-hole, the deodorizing filter unit is detached from the door, a new deodorizing filter unit is installed in the door, and the door is inserted into the through-hole, thereby completing replacement.

However, since such a deodorizing filter unit only serves to remove a bad smell, for sterilization, anti-bacterial and insect-proof functions, air-purification, etc. in or around a bidet, a separate filter or a sterilizing solution is required.

CITED DOCUMENT

Patent Document

Korean Patent Publication No. 10-1057447

SUMMARY OF THE INVENTION

Accordingly, the present invention has been made keeping in mind the above problems occurring in the related art, and the present invention is intended to propose a clarifier for bidet with phytoncide filter which uses a phytoncide filter unit to provide the bad smell removal/deodorization, anti-bacterial and insect-proof functions in a bidet, as well as to provide a pleasant feeling to a user.

In order to achieve the above object, according to one aspect of the present invention, the invention provides a clarifier for bidet with phytoncide filter, including: a base; a blower sucking air into the bidet; a filter casing mounted to the base; a phytoncide filter unit contained in the filter casing; a door to open and close the filter casing; and a duct connecting the blower and the filter casing to each other.

In an embodiment, the invention provides a clarifier for bidet with phytoncide filter, wherein the phytoncide filter unit includes: a filter part; a body part having a longitudinal through-hole; a recess part provided at a front side of the body part to accommodate the filter part; a storage part provided at an upper or lower portion of the body part to store a mass of phytoncide therein; and a hole part communicatingly connecting the storage part and the front side of the body part.

In an embodiment, the invention provides a clarifier for bidet with phytoncide filter, wherein the storage part has: a storage recess with an upper or lower side opened; and a cover opening and closing the storage recess, the storage recess having a stepped groove at an upper or lower front side thereof.

The present invention has the following effects.

The phytoncide filter unit deodorizes the bidet and purifies air in the bidet, so that the purified air provides a bathroom with a pleasant environment and has the effects of exterminating mold or insects such as dust mites in a room or a bathroom, and an anti-bacterial effect whereby the bidet is resistant to bacteria such as colon bacillus, pseudomonas aeruginosa, or the like.

Further, since phytoncide is stored in a recess-type storage part blocked by a partition, the phytoncide does not come into contact with air passing through a through-hole, so the phytoncide can be used long-term.

Furthermore, since a recess part for mounting a filter unit is provided with a stepped groove, air passes through the filter unit while flowing through the stepped groove as well as through the through-hole, thereby considerably improving filter efficiency.

BRIEF DESCRIPTION OF THE DRAWINGS

The above and other objects, features and advantages of the present invention will be more clearly understood from the following detailed description when taken in conjunction with the accompanying drawings, in which.

DETAILED DESCRIPTION OF THE INVENTION

Figure 1:
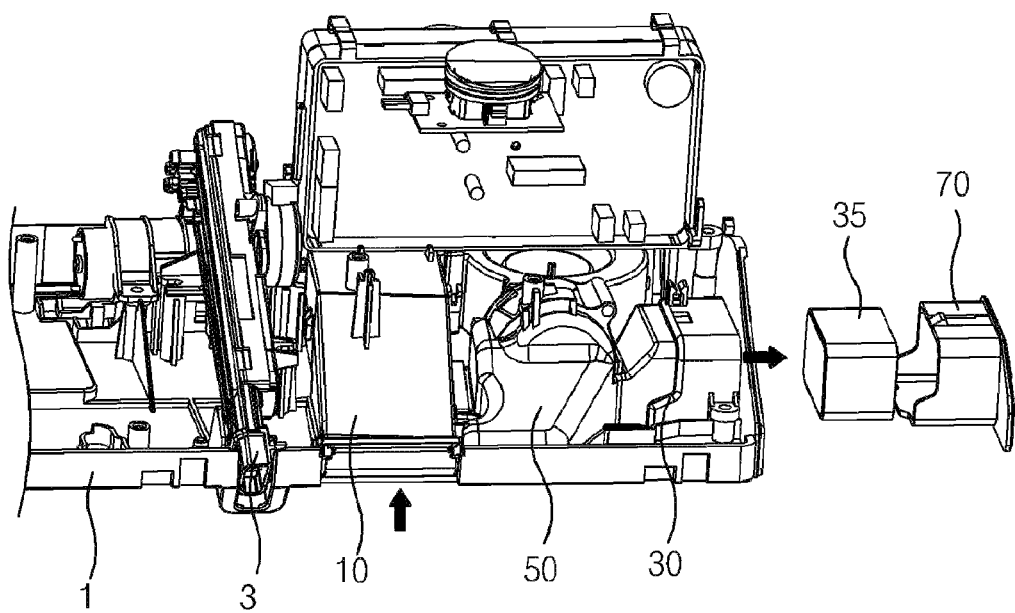
FIG. 1 is a perspective view showing a filtering device for a bidet in which a phytoncide filter unit is contained according to an embodiment of the present invention.

Reference will now be made in greater detail to a preferred embodiment of the invention, an example of which is illustrated in the accompanying drawings. Wherever possible, the same reference numerals will be used throughout the drawings and the description to refer to the same or like parts.

FIG. 1 is a perspective view showing a filtering device for a bidet in which a phytoncide filter unit is contained according to an embodiment of the present invention.

As shown in FIG. 1, the filtering device for a bidet includes a blower 10, a filter casing 30 having a phytoncide filter unit 35 therein, a duct 50 which connects the blower 10 and the filter casing 30, and a door 70 which opens and closes the filter casing 30.

The blower 10, the filter casing 30, and the duct 50 are mounted to a base 1 of a housing of the filtering device.

An intake port of the blower 10 is disposed in a through-hole (not shown) formed in the base 1. The through-hole faces the inside of a bidet.

The door 70 is detachably mounted to the filter casing 30 such that the phytoncide filter unit 35 can be conveniently replaced.

A cover (not shown) is fastened to an upper surface of the base 1.

A nozzle 3 is mounted to the base 1, and a nozzle assembly is disposed around the nozzle 3.

Phytoncides are the organic compounds (terpene) that plants produce to protect themselves from harmful insects and germs. Phytoncides serve to protect the human body from toxins and also have an antibacterial function.

Phytoncides quickly and strongly react with harmful substances, such as formaldehyde, benzene, toluene, xylene, carbon monoxide, acetaldehyde, or the like, that are indoor noxious gases in order to deodorize them and decompose odor causing materials.

Thus, phytoncides have the effects of bad smell removal/deodorization, and anti-bacterial and insect-proof functions, while providing a pleasant scent.

The pleasant scent is the natural scent of plants, which provides humans with a pleasant sensation and contributes to the stabilization of autonomic nerves and psychological, physical relaxation. Further, when a person breathes terpene-mixed air, the air is purified, so the cardiopulmonary functions of the person can be improved. Further, phytoncides also contribute to both an increase in anions in the body, which helps to clean blood, and waste emission from the body.

Phytoncides serve to purify air by deodorizing and removing bad smells of four representative bad-smell materials (ammonia, hydrogen sulfide, trimetalamine, and methyl mercaptan which give out bad odors such as the smells of rotten fish or vegetable) and indoor noxious gases (benzene, toluene, xylene, carbon monoxide, acetaldehyde).

Phytoncides also serve to exterminate mold or dust mites in a room, such as a bathroom, and to provide resistance against bacteria such as colon bacillus, pseudomonas aeruginosa, or the like.

With the employment of a filter unit containing such phytoncides having the above-mentioned functions and effects to a bidet, of the environment in which the bidet exists becomes pleasant and has anti-bacterial and insect-proof effects.

Phytoncide ingredients in the filter unit 35 may preferably be prepared as a fine powder.

Figure 2:
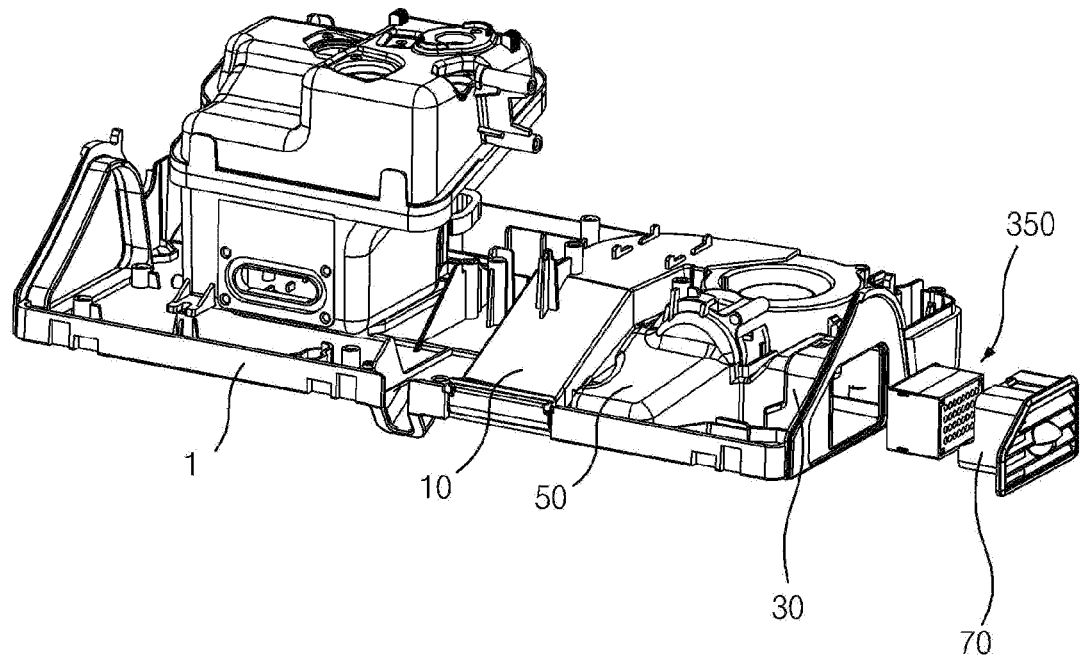
FIGS. 2 and 3 are perspective views showing the filtering device for a bidet in which a phytoncide filter unit of another embodiment is dissembled and assembled.
Figure 3:
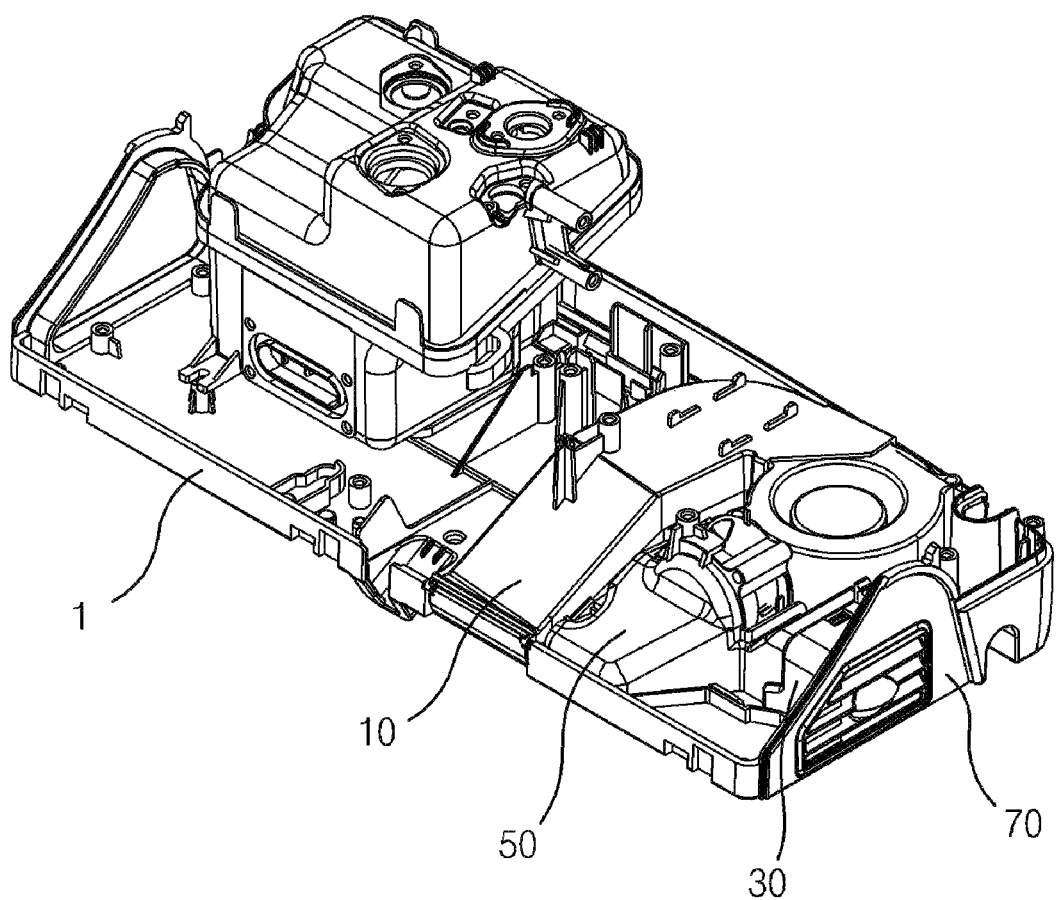
Figure 4:
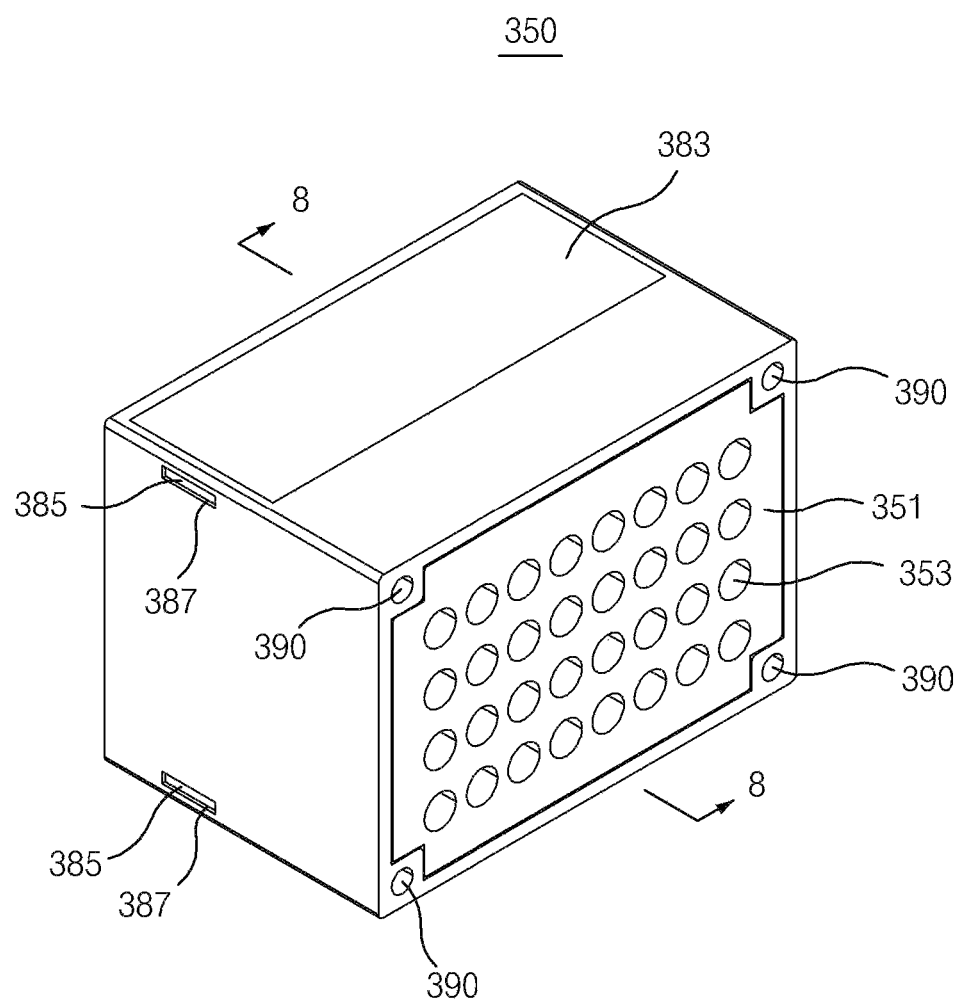
FIG. 4 is a front perspective view showing the phytoncide filter unit of FIG. 2.

FIGS. 2 and 3 are perspective views showing the filtering device for a bidet in which a phytoncide filter unit of another embodiment is dissembled and assembled.

As shown in FIGS. 4 to 8, a phytoncide filter unit 350 includes a filter part 351, a body part 360 having a longitudinal through-hole 365, a recess part 370 which is provided at a front side of the body part 360 to mount the filter part 351, a storage part 380 which is provided at an upper or lower portion 361 or 363 of the body part 360 to store the ingredient of phytoncide, and a hole part 390 which communicatingly connects the storage part 380 and the front side of the body part 360.

The filter part 351 is an unwoven fabric pad that is a rectangular deodorizing filter that contains activated carbon and zeolite. The filter part has a plurality of holes 353 through which air passes and is filtered.

The body part 360 is of a cubic form through which the longitudinal through-hole 365 extends at the center thereof.

The front side of the body part 360 has the recess part 370 in which the filter part 351 is mounted.

The recess part 370 has stepped grooves 371 and 373 at upper and lower front sides thereof, respectively.

Figure 5:
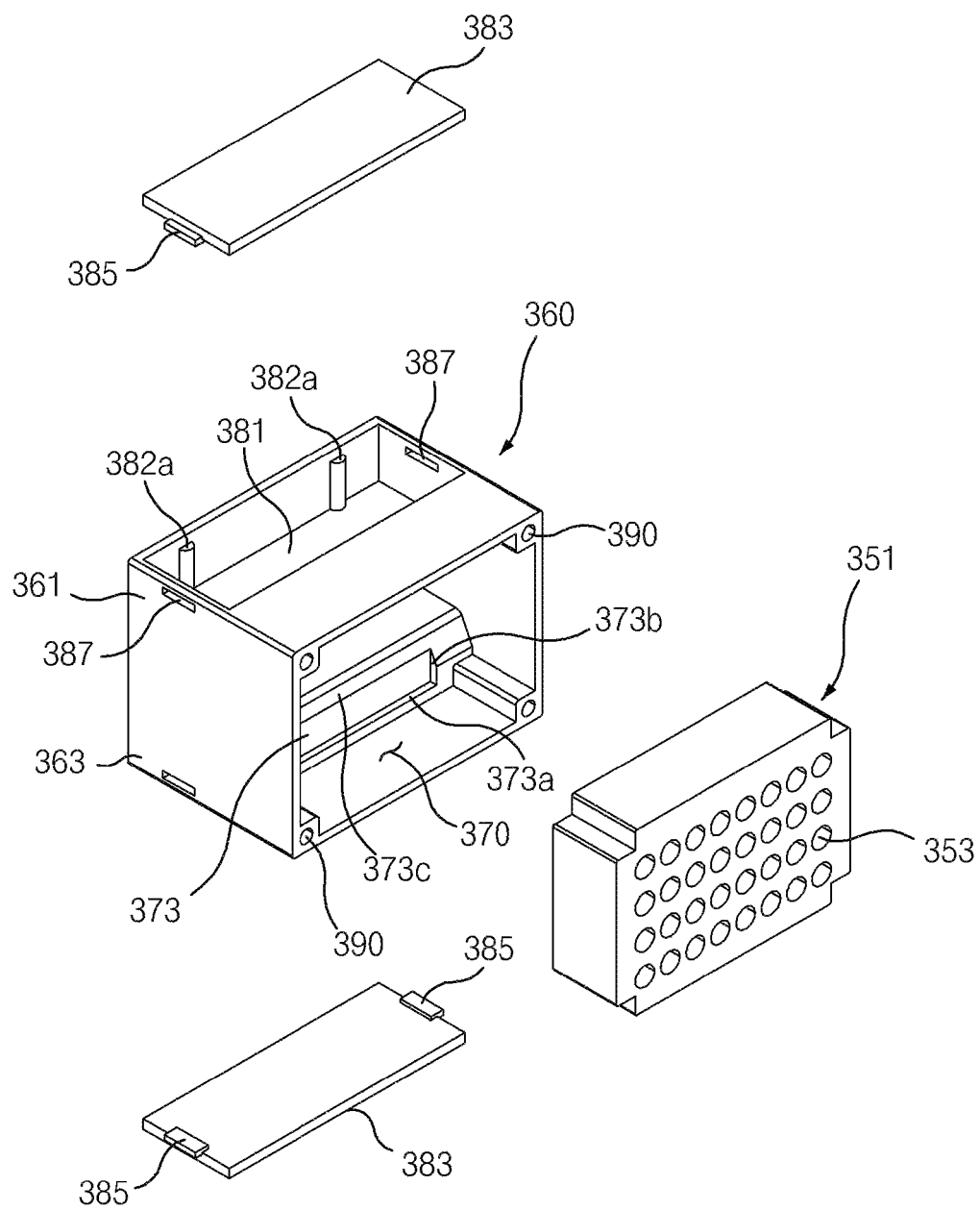
FIG. 5 is an exploded perspective view of FIG. 4.
Figure 6:
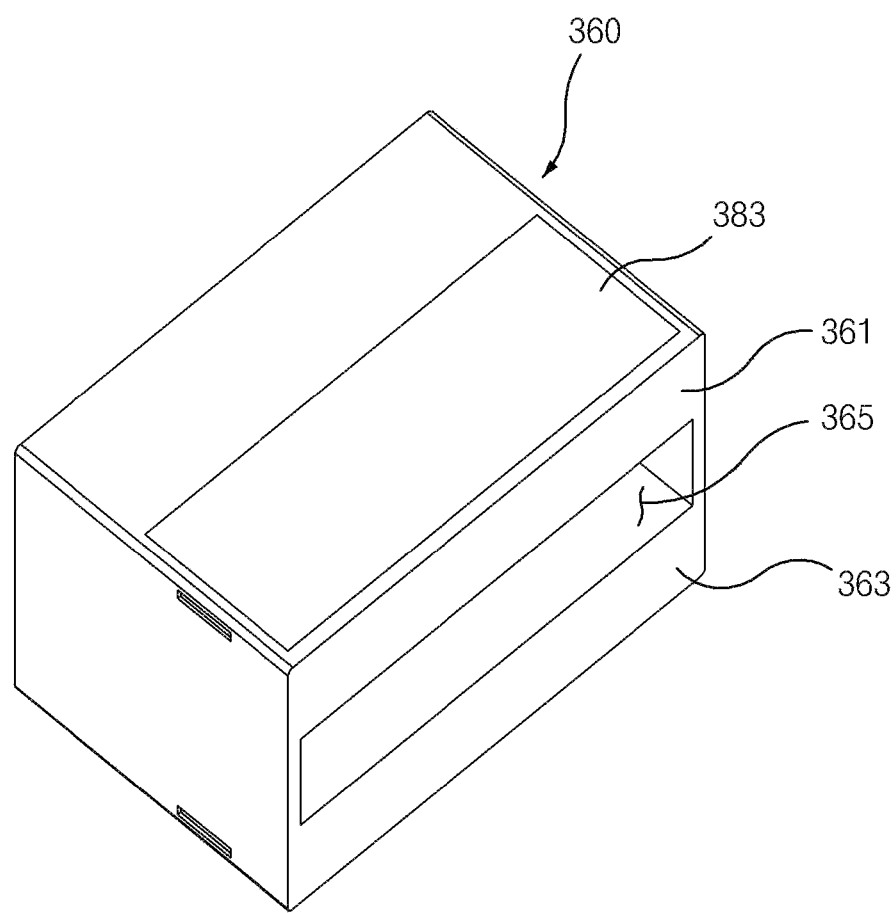
FIG. 6 is a bottom perspective view of FIG. 4.
Figure 7:
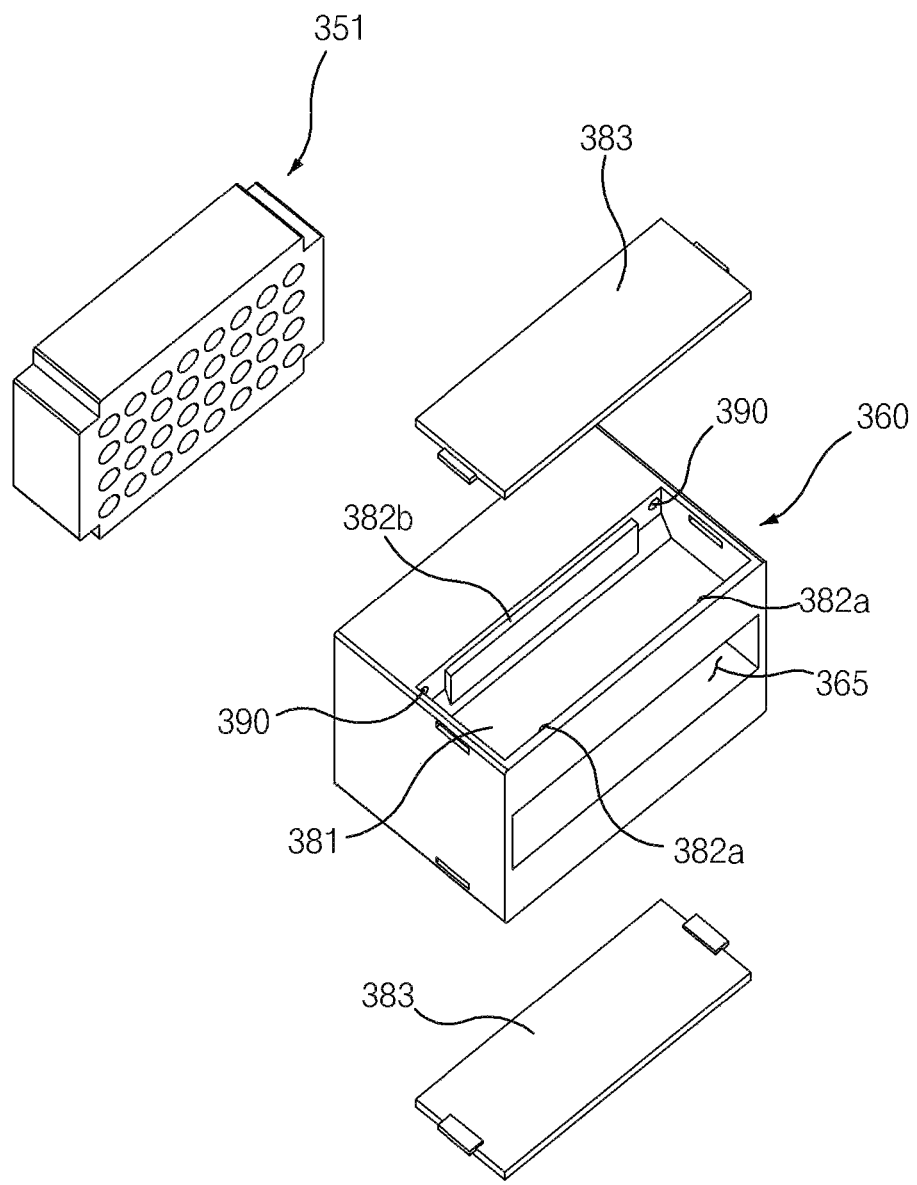
FIG. 7 is an exploded perspective view of FIG. 6.
Figure 8:
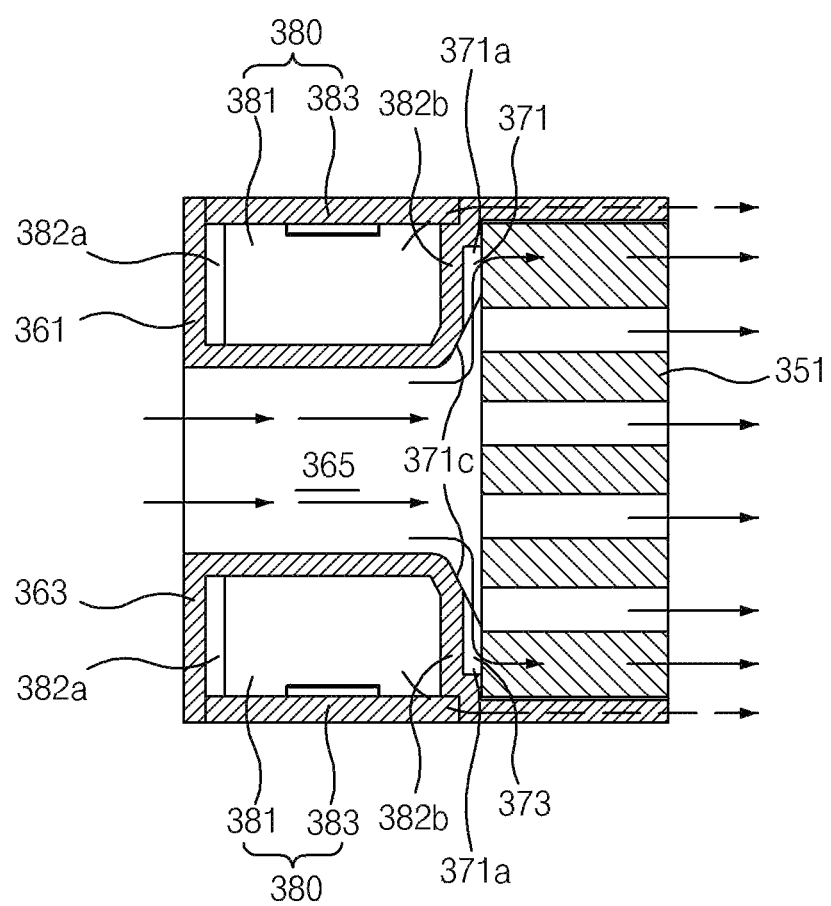
FIG. 8 is a sectional view taken along line 8-8 of FIG. 4.

As shown in FIGS. 5 and 8, the stepped groove 373 is a groove that consists of a bottom step 373a, a side step 373b, and an upper inclined portion 373c, defining a space by the bottom side and lateral sides.

Similarly, the stepped groove 371 is a groove that consists of an upper step 371a, a side step 371b, and a lower inclined portion 371c, defining a space by the upper side and lateral sides.

Thus, air (the arrow of solid line) flowing through the through-hole 365 passes through both a central portion of the filter part 351 and an outer portion of the filter part through the stepped grooves 371 and 373 along the inclined portions 371c and 373c. That is, air uniformly passes through the entire surface of the filter part, so that durability and filtering efficiency of the filter part can be considerably improved.

The body part 360 is divided into upper and lower portions 361 and 363 from the through-hole 365.

The upper and lower portions 361 and 363 of the body part 360 are provided with storage parts 380 containing the ingredient of phytoncide.

The storage part 380 has a storage recess 381 with upper or lower side opened, and a cover 383 which opens or closes the storage recess 381.

The storage recess 381 is defined from the through-hole 365 by a partition wall, so the ingredient of phytoncide contained in the storage recess does not directly contact air passing through the through-hole 365, and thus can be used for a long term.

The cover 383 has protrusions 385 at opposite sides, and the storage recess 381 has grooves 387 into which the protrusions 385 are fitted.

The storage recess 381 has stopper portions 382a and 382b at inner sides thereof.

The stopper portions 382a and 382b serve to restrict a maximum distance at which the cover 383 is lowered, thereby preventing the cover 383 from being excessively lowered and damaged.

The stopper portion 382a may consist of opposite semi-circular rib posts on one inner side of the storage recess.

The stopper portion 382b may have a planar shape that naturally protrudes when forming the stepped grooves 371 and 373.

The hole parts 390 formed on the upper and lower portions 361 and 363 of the body part 360 allow the scent of phytoncide to escape therethrough as indicated by the arrow of dotted line in FIG. 8.

The hole parts 390 are formed at four corners of the front side of the body part.

Thus, the scent of phytoncide escaping from the hole parts 390 flows together with air passing through the filter part 351.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:
1. A clarifier for bidet with phytoncide filter, comprising:
a base;
a blower mounted on the base and sucking air into the bidet;
a filter casing mounted on the base and receiving a phytoncide filter therein;
a door opening and closing the filter casing to replace the phytoncide filter; and a duct disposed between the blower and the filter casing and connecting the blower and the filter casing to each other, wherein the air flows from the blower to the phytoncide filter via the duct, wherein the phytoncide filter comprises:

a body part;

a first storage part provided at a duct side upper portion of the body part to store a mass of phytoncide therein, wherein a first through-hole is formed in the body part from the storage part toward outside;

a second through-hole formed under the first storage part of the body part;

a recess part formed in the body part and open toward outside;

a filter part received in the recess part, wherein the filter part has a plurality of third through-holes;

wherein the blower, the duct, the second through-hole and the third through-holes form an air-flowing passageway open to outside, and the first through-hole is isolated from the air-flowing passageway.

2. The clarifier for bidet with phytoncide filter according to claim 1, wherein the phytoncide filter unit further comprises:

a second storage part provided at a duct side lower portion of the body part to store a mass of phytoncide therein, wherein a fourth through-hole is formed in the body part from the second storage part toward outside, wherein the second through-hole is formed between the first and second storage parts; and the fourth through-hole is isolated from the air-flowing passageway.

3. The clarifier for bidet with phytoncide filter according to claim 1, wherein the first storage part has:

a storage recess with an upper or lower side opened; and a cover opening and closing the storage recess, the storage recess having a stepped groove at an upper or lower front side thereof.

4. A clarifier for bidet with phytoncide filter, comprising:

a base;

a blower sucking air into the bidet;

a filter casing mounted to the base;

a phytoncide filter unit contained in the filter casing;

a door opening and closing the filter casing to replace the phytoncide filter; and a duct connecting the blower and the filter casing to each other, wherein the phytoncide filter unit comprises:

a filter part;

a body part having a longitudinal through-hole;

a recess part provided at a front side of the body part to accommodate the filter part;

a storage part provided at an upper or lower portion of the body part to store a mass of phytoncide therein; and a hole part communicatingly connecting the storage part and the front side of the body part, wherein the storage part has:

a storage recess with an upper or lower side opened; and a cover opening and closing the storage recess to store the mass of phytoncide, the storage recess having stopper portions at inner sides thereof to restrict a maximum distance at which the cover is lowered and a stepped groove at an upper or lower front side thereof.

* * * * *